(12) United States Patent
Shao et al.

(10) Patent No.: US 11,530,416 B2
(45) Date of Patent: Dec. 20, 2022

(54) PRUNUS PERSICA POLYGALACTURONASE-INHIBITING PROTEIN 1 (PPPGIP1) GENE, AND CLONING METHOD AND USE THEREOF

(71) Applicant: NINGBO UNIVERSITY, Zhejiang (CN)

(72) Inventors: Xingfeng Shao, Zhejiang (CN); Yingying Wei, Zhejiang (CN); Yihui Mao, Zhejiang (CN); Yi Chen, Zhejiang (CN); Shu Jiang, Zhejiang (CN)

(73) Assignee: NINGBO UNIVERSITY, Zhejiang (CN)

( * ) Notice: Subject to any disclaimer, the term of this patent is extended or adjusted under 35 U.S.C. 154(b) by 0 days.

(21) Appl. No.: 17/548,597

(22) Filed: Dec. 13, 2021

(65) Prior Publication Data

US 2022/0186239 A1 Jun. 16, 2022

(30) Foreign Application Priority Data

Dec. 14, 2020 (CN) .......................... 202011465541.3

(51) Int. Cl.
*C12N 15/82* (2006.01)

(52) U.S. Cl.
CPC ..... *C12N 15/8218* (2013.01); *C12N 15/8205* (2013.01)

(58) Field of Classification Search
CPC .................. C12N 15/8205; C12N 15/8218
See application file for complete search history.

(56) References Cited

FOREIGN PATENT DOCUMENTS

WO WO-2007133804 A2 * 11/2007 ............ C07K 14/415

OTHER PUBLICATIONS

He et al (PpVIN2, an acid invertase gene family member, is sensitive to chilling temperature and affects sucrose metabolism in postharvest peach fruit. Plant Growth Regulation 86:169-180, published online Jun. 18, 2018) (Year: 2018).*
Liang et al (Cloning, characterization and expression of the gene encoding polygalacturonase-inhibiting proteins (PGIPs) of peach [*Prunus persica* (L.) Batch], Plant Science 168. 481-486, 2005). (Year: 2005).*
Pan et al (AY903219, published Feb. 2005). (Year: 2005).*
Smith et al (Inheritance and effect on ripening of antisense polygalacturonase genes in transgenic tomatoes. Plant Mol Bio. Mar. 1990;14(3):369-79, 1990) (Year: 1990).*
Wang et al (PpINH1, an invertase inhibitor, interacts with vacuolar invertase PpVIN2 in regulating the chilling tolerance of peach fruit. Horticulture Research 7:168, 1-14, Oct. 2020). (Year: 2020).*
"Prunus persica polygalacturonase-inhibiting protein mRNA, complete cds" GenBank, AY903219.1 downloaded from NCBI-PRIMER (https://www.ncbi.nlm.nih.gov/tools/primer-blast/) on Dec. 13, 2021.
"Polygalacturonase inhibiting protein [Prunus persica]" GenBank, AAQ56728.1 downloaded from NCBI-PRIMER (https://www.ncbi.nlm.nih.gov/tools/primer-blast/) on Dec. 13, 2021.

* cited by examiner

*Primary Examiner* — Charles Logsdon
*Assistant Examiner* — Wayne Zhong
(74) *Attorney, Agent, or Firm* — JCIP Global Inc.

(57) ABSTRACT

The present invention discloses a *Prunus persica* polygalacturonase-inhibiting protein 1 (PpPGIP1) gene, and a cloning method and use thereof. The *Prunus persica* polygalacturonase-inhibiting protein 1 PpPGIP1 gene has a nucleotide sequence shown in SEQ ID NO: 1, and a protein encoded by the *Prunus persica* polygalacturonase-inhibiting protein 1 (PpPGIP1) gene has an amino acid sequence shown in SEQ ID NO: 2. The cloning method includes the following steps: (1) extracting total RNA from a peach, and subjecting the total RNA to reverse transcription to obtain cDNA, which serves as a template; (2) designing primers based on the PpPGIP1 gene sequence; and (3) Polymerase Chain Reaction (PCR) amplification: conducting PCR amplification to obtain a PpPGIP1 gene amplification product.

4 Claims, 2 Drawing Sheets

Specification includes a Sequence Listing.

SEQUENCE LISTING

```
<160> NUMBER OF SEQ ID NOS: 11

<210> SEQ ID NO 1
<211> LENGTH: 993
<212> TYPE: DNA
<213> ORGANISM: Prunus persica
<220> FEATURE:
<221> NAME/KEY: misc_feature
<222> LOCATION: (1)..(993)
<223> OTHER INFORMATION: Full-length peach acid invertase inhibitor gene

<400> SEQUENCE: 1
atggacgtca agttccccac cctcctctgc ttgaccctac tcttctccac catcctaaac      60
caagcgctct ccgagctctg caacccggaa gacaagaaag ttctcctaca aatcaagaaa     120
gccttcaacg acccctacgt cttgacctca tggaagccag agacagactg ctgtgactgg     180
tactgtgtca cctgtgactc caccacaaac cgcatcaact ccctcaccat cttctctggc     240
caagtctccg gtcaaattcc gacccaagtc ggtgacttgc cgtatcttga aacacttgag     300
tttcacaagc aacccaatct taccggacca atacaaccct ccattgccaa gcttaagcgc     360
ctcaaggagc tgcgcctcag ctggactaac atctcaggct ctgtacctga cttcctcagc     420
caactcaaga acctcacctt tcttgacctc tcattcagta acctcacagg ctccatcccc     480
agctcgcttt ctcagcttcc caacctcaac gctcttcatc tagaccgtaa caagctcaca     540
ggtcatattc cgaagtcatt tggagaattc catggcagtg ttccagagct ctatctctcc     600
cacaaccagc tctcaggcaa cataccaacc tcattagcca aactggactt caaccgcata     660
gacttctccc ggaacaagct cgaaggcgat gcatccatga tctttggatt gaacaagaca     720
acccagattg tggatctgtc taggaacttg ctggaattta atctgtcaaa ggtggagttt     780
tccaagagct tgatatcgtt ggatcttaac cataacaaga tcacaggcgg aattccggtg     840
gggctgaccc aagtggattt gcagttcctg aacgtgagct acaacaggtt gtgtggtcag     900
attccagtgg gcgggaagtt acagagcttc gactcctcaa cttatttcca taaccgctgc     960
ttgtgtggtg ctccactccc aagctgcaaa taa                                   993

<210> SEQ ID NO 2
<211> LENGTH: 330
<212> TYPE: PRT
<213> ORGANISM: Prunus persica
<220> FEATURE:
<221> NAME/KEY: MISC_FEATURE
<222> LOCATION: (1)..(330)
```

<223> OTHER INFORMATION: Protein encoded by peach acid invertase
inhibitor gene

<400> SEQUENCE: 2

Met Asp Val Lys Phe Pro Thr Leu Leu Cys Leu Thr Leu Leu Phe Ser
1               5                   10                  15

Thr Ile Leu Asn Gln Ala Leu Ser Glu Leu Cys Asn Pro Glu Asp Lys
            20                  25                  30

Lys Val Leu Leu Gln Ile Lys Lys Ala Phe Asn Asp Pro Tyr Val Leu
        35                  40                  45

Thr Ser Trp Lys Pro Glu Thr Asp Cys Cys Asp Trp Tyr Cys Val Thr
    50                  55                  60

Cys Asp Ser Thr Thr Asn Arg Ile Asn Ser Leu Thr Ile Phe Ser Gly
65                  70                  75                  80

Gln Val Ser Gly Gln Ile Pro Thr Gln Val Gly Asp Leu Pro Tyr Leu
                85                  90                  95

Glu Thr Leu Glu Phe His Lys Gln Pro Asn Leu Thr Gly Pro Ile Gln
            100                 105                 110

Pro Ser Ile Ala Lys Leu Lys Arg Leu Lys Glu Leu Arg Leu Ser Trp
        115                 120                 125

Thr Asn Ile Ser Gly Ser Val Pro Asp Phe Leu Ser Gln Leu Lys Asn
    130                 135                 140

Leu Thr Phe Leu Asp Leu Ser Phe Ser Asn Leu Thr Gly Ser Ile Pro
145                 150                 155                 160

Ser Ser Leu Ser Gln Leu Pro Asn Leu Asn Ala Leu His Leu Asp Arg
                165                 170                 175

Asn Lys Leu Thr Gly His Ile Pro Lys Ser Phe Gly Glu Phe His Gly
            180                 185                 190

Ser Val Pro Glu Leu Tyr Leu Ser His Asn Gln Leu Ser Gly Asn Ile
        195                 200                 205

Pro Thr Ser Leu Ala Lys Leu Asp Phe Asn Arg Ile Asp Phe Ser Arg
    210                 215                 220

Asn Lys Leu Glu Gly Asp Ala Ser Met Ile Phe Gly Leu Asn Lys Thr
225                 230                 235                 240

Thr Gln Ile Val Asp Leu Ser Arg Asn Leu Leu Glu Phe Asn Leu Ser
                245                 250                 255

Lys Val Glu Phe Ser Lys Ser Leu Ile Ser Leu Asp Leu Asn His Asn
            260                 265                 270

Lys Ile Thr Gly Gly Ile Pro Val Gly Leu Thr Gln Val Asp Leu Gln
        275                 280                 285

Phe Leu Asn Val Ser Tyr Asn Arg Leu Cys Gly Gln Ile Pro Val Gly
    290                 295                 300

Gly Lys Leu Gln Ser Phe Asp Ser Ser Thr Tyr Phe His Asn Arg Cys
305                 310                 315                 320

Leu Cys Gly Ala Pro Leu Pro Ser Cys Lys
                325                 330

<210> SEQ ID NO 3
<211> LENGTH: 22
<212> TYPE: DNA
<213> ORGANISM: Artificial sequence
<220> FEATURE:
<223> OTHER INFORMATION: PpPGIP1 gene upstream primer sequence

<400> SEQUENCE: 3
cccgcaatca catttcttat cc                                      22

<210> SEQ ID NO 4
<211> LENGTH: 20
<212> TYPE: DNA
<213> ORGANISM: Artificial sequence
<220> FEATURE:
<223> OTHER INFORMATION: PpPGIP1 gene downstream primer sequence

<400> SEQUENCE: 4
cactcccaag ctgcaaataa         20

<210> SEQ ID NO 5
<211> LENGTH: 46
<212> TYPE: DNA
<213> ORGANISM: Artificial sequence
<220> FEATURE:
<223> OTHER INFORMATION: pGBKT7-PpVIN2-F

<400> SEQUENCE: 5
aggccgaatt cccggggatc catggcagac ccaagacctt ttcttc         46

<210> SEQ ID NO 6
<211> LENGTH: 41
<212> TYPE: DNA
<213> ORGANISM: Artificial sequence
<220> FEATURE:
<223> OTHER INFORMATION: pGBKT7-PpVIN2-R

<400> SEQUENCE: 6
ctagttatgc ggccgctgca gcatgaacga aatcgaaatc g         41

<210> SEQ ID NO 7
<211> LENGTH: 43
<212> TYPE: DNA
<213> ORGANISM: Artificial sequence
<220> FEATURE:
<223> OTHER INFORMATION: pGADT7-PpPGIP1-F

<400> SEQUENCE: 7
gtgggcatcg atacgggatc ccccgcaatc acatttctta tcc         43

<210> SEQ ID NO 8
<211> LENGTH: 41
<212> TYPE: DNA
<213> ORGANISM: Artificial sequence
<220> FEATURE:
<223> OTHER INFORMATION: pGADT7-PpPGIP1-R

<400> SEQUENCE: 8
acgattcatc tgcagctcga gttatttgca gcttgggagt g         41

<210> SEQ ID NO 9
<211> LENGTH: 41
<212> TYPE: DNA
<213> ORGANISM: Artificial sequence
<220> FEATURE:
<223> OTHER INFORMATION: pTRV2-PpPGIP1-F

<400> SEQUENCE: 9
aaggttaccg aattctctag agacccctac gtcttggcct c         41

<210> SEQ ID NO 10
<211> LENGTH: 44
<212> TYPE: DNA
<213> ORGANISM: Artificial sequence
<220> FEATURE:

```
<223> OTHER INFORMATION: pTRV2-PpPGIP1-R

<400> SEQUENCE: 10
tgtcttcggg acatgcccgg gcttgagttg gctgaggaag tcag            44

<210> SEQ ID NO 11
<211> LENGTH: 300
<212> TYPE: DNA
<213> ORGANISM: Artificial sequence
<220> FEATURE:
<223> OTHER INFORMATION: PpPGIP1-specific silencing sequence

<400> SEQUENCE: 11
gacccctacg tcttggcctc atgggaccca gagacagact gctgtgactg gtactctgtc      60
acctgtgact ccaccacaaa ccgcgtcaac tccctcaccc tcttctccgg gggactctcc     120
ggtcaaattc cgacccaagt cggtgacttg ccgtatcttg aaacacttga gtttcacaag     180
caacccaatc ttaccggacc aatccaaccc tccattgcca agcttaagcg cctcaaggag     240
ctgcgcctca gctggaccaa catctccggc tctgtccctg acttcctcag ccaactcaag     300
```

PRUNUS PERSICA POLYGALACTURONASE-INHIBITING PROTEIN 1 (PPPGIP1) GENE, AND CLONING METHOD AND USE THEREOF

CROSS-REFERENCE TO RELATED APPLICATION

This application claims the priority benefit of China application serial no. 202011465541.3, filed on Dec. 14, 2020. The entirety of the above-mentioned patent application is hereby incorporated by reference herein and made a part of this specification.

BACKGROUND OF THE INVENTION

1. Technical Field

The present invention belongs to the field of plant molecular biology, and particularly relates to a *Prunus persica* polygalacturonase-inhibiting protein 1 (PpPGIP1) gene that regulates a *Prunus persica* vacuolar invertase 2 (PpVIN2), and a cloning method and use thereof.

2. Background Art

*Prunus persica*, a species in the family Rosaceae, is prone to cold damage at 2° C. to 8° C., and main symptoms include fruit browning, failure of normal after-ripening, shrinkage of subcutaneous cells to a spongy shape, inherent flavor loss, and the like. Low temperature stress is often accompanied by changes in the contents of soluble sugars and the activities of metabolism-related enzymes. In plants, sucrose is the strongest cell cryoprotectant, which protects plants by adjusting an osmotic pressure, maintaining a liquid crystal state of a cell membrane bilayer, and stabilizing proteins. Previous studies have shown that, under low temperature stress, the degradation of sucrose in peaches increases, and the enhancement of membrane stability and cold tolerance is closely related to the increase of a sucrose level. The vacuolar invertase (VIN) is a key enzyme for sucrose metabolism and sugar signaling, which can irreversibly hydrolyzes sucrose into glucose and fructose, thereby helping to establish and maintain the osmotic potential of cells, and playing important roles in plant development and response to various stresses. Early studies have shown that PpVIN2 is the only cold-responsive VIN gene, and its expression is significantly induced by cold, and PpVIN2 plays an important upregulation role in the activity of VIN after cold storage, and is negatively correlated with a sucrose content.

The yeast two-hybrid system (Y2H) is a system where two proteins to be studied are cloned (fused) into a DNA binding domain (DNA-BD) and a transcription activation domain (AD) of a transcriptional activator (such as GAL4) of a yeast expression plasmid respectively to construct a fusion expression vector, and then the interaction between the two proteins is analyzed according to the expression product and the chromogenic reaction. The yeast two-hybrid system can be used to effectively screen out interacting proteins of PpVIN2.

Transient expression is a technique where a target gene is introduced into a live plant through a specific plant expression vector and then the target gene is expressed in a short period of time (up to several days), which can accurately reflect the function of a gene, and is widely used in promoter analysis, protein interaction, and gene function analysis. Virus-induced gene silencing (VIGS) is a technique where a virus carrying a target gene fragment infects a plant to induce the silencing of an endogenous gene in the plant and cause a phenotypic variation, and then the function of the target gene is studied according to the phenotypic variation. The *Agrobacterium* transformation method is simple, fast, safe, and effective, and can lead to a high expression level. The successful transient silencing of PpPGIP1 in peaches has not been achieved. Therefore, the transient silencing of the target gene PpPGIP1 in peaches through *Agrobacterium* transformation is particularly important for the function analysis and application of the gene.

SUMMARY OF THE INVENTION

A technical problem to be solved by the present invention is to provide a *Prunus persica* polygalacturonase-inhibiting protein 1 (PpPGIP1) gene that up-regulates a *Prunus persica* vacuolar invertase 2 (PpVIN2) and participates in sucrose metabolism, and a cloning method and use thereof.

In order to solve the above technical problem, the present invention adopts the following technical solutions: A *Prunus persica* polygalacturonase-inhibiting protein 1 (PpPGIP1) gene is provided, with a nucleotide sequence shown in SEQ ID NO: 1.

A protein encoded by the *Prunus persica* polygalacturonase-inhibiting protein 1 (PpPGIP 1) gene described above is provided, with an amino acid sequence shown in SEQ ID NO: 2.

A cloning method of the *Prunus persica* polygalacturonase-inhibiting protein 1 (PpPGIP1) gene described above is provided, including the following steps:

(1) extracting total RNA from a peach, and subjecting the total RNA to reverse transcription to obtain cDNA, which serves as a template;

(2) designing primers based on the PpPGIP1 gene sequence: upstream primer sequence: 5'-CCCGCAATCACATTTCTTATCC-3' (SEQ ID NO: 3), and downstream primer sequence: 5'-CACTCCCAAGCTGCAAATAA-3' (SEQ ID NO: 4); and (3) Polymerase Chain Reaction (PCR) amplification: conducting PCR amplification to obtain a PpPGIP1 gene amplification product.

Use of the *Prunus persica* polygalacturonase-inhibiting protein 1 (PpPGIP1) gene described above in the preparation of a peach antifreeze is provided.

Use of the *Prunus persica* polygalacturonase-inhibiting protein 1 (PpPGIP1) gene described above in the preparation of a *Prunus persica* vacuolar invertase 2 (PpVIN2) inhibitor is provided.

In the use of the *Prunus persica* polygalacturonase-inhibiting protein 1 (PpPGIP1) gene in the preparation of a *Prunus persica* vacuolar invertase 2 (PpVIN2) inhibitor described above, a virus-induced *Prunus persica* polygalacturonase-inhibiting protein 1 (PpPGIP1) gene silencing system is constructed in peach through *Agrobacterium* transient transformation to obtain peach in which the activity of the vacuolar invertase (VIN) is effectively inhibited.

Compared with the prior art, the present invention has the following advantages:

1. It is confirmed for the first time that the *Prunus persica* polygalacturonase-inhibiting protein 1 (PpPGIP1) can bind to the acid invertase PpVIN2 and up-regulate its activity, thereby affecting the catabolism of sucrose.

2. A VIGS system for PpPGIP1 is successfully constructed in peach for the first time. In "Yulu" peach in which the expression of PpPGIP1 is effectively reduced, the activity of the vacuolar invertase (VIN) can be effectively inhibited, and the decomposition of sucrose can be reduced to maintain the role of sucrose as an antifreeze and the ability of sucrose to adjust an osmotic pressure, such that the peach has high cold tolerance and the cold damage during storage and transportation is reduced.

In summary, the cloning and use of the key gene PpPGIP1 that regulates the *Prunus persica* vacuolar invertase 2 (PpVIN2) in the present invention confirm that there is a protein-protein interaction relationship between PpPGIP1 and PpVIN2, and the silencing of the target gene PpPGIP1 in peach through *Agrobacterium* transient transformation can significantly inhibit the activity of PpVIN2. PpPGIP1 has an effective function in a PpVIN2-mediated sucrose metabolism process, and can be used in the improvement of peach varieties in terms of improving the cold tolerance.

DETAILED DESCRIPTION OF THE EMBODIMENTS

The present invention will be described in further detail below with reference to the accompanying drawings and examples.

Specific Example 1

Cloning and sequence analysis of *Prunus persica* polygalacturonase-inhibiting protein 1 (PpPGIP1) gene 1. Total RNA was extracted from "Yulu" peach and reverse-transcribed into cDNA, which would serve as a PCR template. Specifically: RNA prep Pure Plant Kit of TIANGEN (Tiangen, Beijing, China) was used to extract total RNA from peach, and then the HiScript® II Q Select RT Super Mix for qPCR (Vazyme, Nanjing, China) kit was used to reverse-transcribe the total RNA into cDNA, which would serve as a template for PCR.

2. The online website NCBI-PRIMER (https://www.ncbi.nlm.nih.gov/tools/primer-blast/) was used to design specific amplification primers for a CDS region of the peach PpPGIP1 gene (Gene ID: LOC18769194): upstream primer sequence: 5'-CCCGCAATCACATTTCTTATCC-3' (SEQ ID NO: 3), and downstream primer sequence: 5'-CACTCCCAAGCTGCAAATAA-3' (SEQ ID NO: 4).

3. PCR amplification: PCR amplification was conducted to obtain a PpPGIP1 gene amplification product. A PCR amplification system included: 2 μL of cDNA, 12.5 μL of 2× Phanta Max Master Mix (PCR amplification high-fidelity enzyme: 2× Phanta Max Master Mix was purchased from Nanjing Vazyme Biotech Co., Ltd.), 1 μL of each of the upstream and downstream primers, and 8.5 μL of ddH$_2$O. A PCR amplification procedure was as follows: pre-denaturation at 95° C. for 3 min; denaturation at 95° C. for 15 s, annealing at 60° C. for 15 s, and extension at 72° C. for 1 min, 35 cycles; and complete extension at 72° C. for 5 min.

4. Colony PCR and sequence alignment: The PCR amplification product was extracted and purified, and then ligated to a PMD18-T vector, the vector was transformed into *Escherichia coli* (*E. coli*) DH5α, and then the *E. coli* was coated on an LB-Amp plate that was evenly coated with X-Gal and IPTG, and then invertedly cultivated overnight at 37° C. After further verification by PCR, sequencing was conducted to obtain the PpPGIP1 sequence, which matched the peach genome data and was shown in SEQ ID NO: 1:

ATGGACGTCAAGTTCCCCACCCTCCTCTGCTTGACCCTACTCTTCTCCAC
CATCCTAAACCAAGCGCTCTCCGAGCTCTGCAACCCGGAAGACAAGAAAG
TTCTCCTACAAATCAAGAAAGCCTTCAACGACCCCTACGTCTTGACCTCA
TGGAAGCCAGAGACAGACTGCTGTGACTGGTACTGTGTCACCTGTGACTC
CACCACAAACCGCATCAACTCCCTCACCATCTTCTCTGGCCAAGTCTCCG
GTCAAATTCCGACCCAAGTCGGTGACTTGCCGTATCTTGAAACACTTGAG
TTTCACAAGCAACCCAATCTTACCGGACCAATACAACCCTCCATTGCCAA
GCTTAAGCGCCTCAAGGAGCTGCGCCTCAGCTGGACTAACATCTCAGGCT
CTGTACCTGACTTCCTCAGCCAACTCAAGAACCTCACCTTTCTTGACCTC
TCATTCAGTAACCTCACAGGCTCCATCCCCAGCTCGCTTTCTCAGCTTCC
CAACCTCAACGCTCTTCATCTAGACCGTAACAAGCTCACAGGTCATATTC
CGAAGTCATTTGGAGAATTCCATGGCAGTGTTCCAGAGCTCTATCTCTCC
CACAACCAGCTCTCAGGCAACATACCAACCTCATTAGCCAAACTGGACTT
CAACCGCATAGACTTCTCCCGGAACAAGCTCGAAGGCGATGCATCCATGA
TCTTTGGATTGAACAAGACAACCCAGATTGTGGATCTGTCTAGGAACTTG
CTGGAATTTAATCTGTCAAAGGTGGAGTTTTCCAAGAGCTTGATATCGTT
GGATCTTAACCATAACAAGATCACAGGCGGAATTCCGGTGGGGCTGACCC
AAGTGGATTTGCAGTTCCTGAACGTGAGCTACAACAGGTTGTGTGGTCAG
ATTCCAGTGGGCGGGAAGTTACAGAGCTTCGACTCCTCAACTTATTTCCA
TAACCGCTGCTTGTGTGGTGCTCCACTCCCAAGCTGCAAATAA.

A protein encoded by the peach acid invertase inhibitor gene PpPGIP1 had an amino acid sequence shown in SEQ ID NO: 2:

MDVKFPTLLCLTLLFSTILNQALSELCNPEDKKVLLQIKKAFNDPYVLTS
WKPETDCCDWYCVTCDSTTNRINSLTIFSGQVSGQIPTQVGDLPYLETLE
FHKQPNLTGPIQPSIAKLKRLKELRLSWTNISGSVPDFLSQLKNLTFLDL
SFSNLTGSIPSSLSQLPNLNALHLDRNKLTGHIPKSFGEFHGSVPELYLS
HNQLSGNIPTSLAKLDFNRIDFSRNKLEGDASMIFGLNKTTQIVDLSRNL
LEFNLSKVEFSKSLISLDLNHNKITGGIPVGLTQVDLQFLNVSYNRLCGQ
IPVGGKLQSFDSSTYFHNRCLCGAPLPSCK.

Bioinformatics analysis showed that the PpPGIP1 protein included 330 amino acid residues (AA), and had a molecular weight of 36.5 kDa and a theoretical isoelectric point (pI) of 8.03. According to the secondary structure prediction, in the PpPGIP1 protein, α-helix accounted for 32.73%, β-pleated sheet accounted for 11.52%, and random coil between α-helix and β-pleated sheet accounted for 55.76%. Most of the AA residues of the PpPGIP1 polypeptide chain were below 0, and the entire peptide chain was hydrophilic. Therefore, it was inferred that the PpPGIP1 protein was a hydrophilic protein. There was no transmembrane domain in the PpPGIP1 protein, and 1-330AA was completely on the cell membrane surface. Therefore, it was inferred that the protein was an outer membrane protein (OMP). The protein signal peptide prediction showed that, in the PpPGIP1 protein, there were 24 AA signal peptide sequences at the N-terminus, and cleavage sites were located between the 24th serine (Ser) and the 25th glutamic acid (Glu). The PpPGIP1 protein included 7 N-glycosylation sites, which were located at AA 106, 130, 144, 154, 238, 254, and 291, respectively. The PpPGIP1 protein included 12 phosphorylation sites, including 9 Ser sites and 3 Thr sites. The tertiary structure prediction showed that, in the PpPGIP1 protein, there were 4 strictly conserved cysteine residues at each of the N-terminus and the C-terminus, and the central region was occupied by an LRR domain rich in leucine repeats.

Specific Example 2

A yeast two-hybrid system (Y2H) was used to confirm the protein-protein interaction between PpPGIP1 and PpVIN2.

1. Construction and identification of a bait recombinant vector pGBKT7-PpVIN2 and a prey recombinant vector pGADT7-PpPGIP1

The online website NCBI-PRIMER (https://www.ncbi.nlm.nih.gov/tools/primer-blast/) was used to design specific amplification primers for the peach PpPGIP1 gene and PpVIN2 gene (with Gene ID: LOC18769194 and Gene ID: LOC18776102, respectively), and the primers each are flanked with an appropriate restriction site and a homologous sequence of an expression vector (Table 1). The primers were designed in accordance with the requirements of the homologous recombinase Clon Express®II One Step Cloning Kit (Vazyme, Nanjing, China) and the high-fidelity enzyme 2× Phanta Max Master Mix (Vazyme, Nanjing, China). Homologous sequences at two termini of a linearized vector were respectively introduced at the 5'-termini of the forward and reverse specific primers of the target fragment, such that the 5'-terminus and 3'-terminus of an amplified target fragment carried homologous sequences (15 to 20 bp) corresponding to the two termini of the linearized expression vector, respectively, thereby ensuring a direction of insertion of the target fragment into the expression vector.

TABLE 1

Primer sequences for constructing the recombinant vectors pGADT7-PpPGIP1 and pGBKT7-PpVIN2

| Primer | Sequence |
| --- | --- |
| pGBKT7-PpVIN2-F (SEQ ID NO: 5) | *AGGCCGAATTCCCGGG*GGATCCATGGCAGACCCAAGACCTTTTCTTC |
| pGBKT7-PpVIN2-R (SEQ ID NO: 6) | *CTAGTTATGCGGCCGC*CTGCAGCATGAACGAAATCGAAATCG |
| pGADT7-PpPGIP1-F (SEQ ID NO: 7) | *GTGGGCATCGATACG*GGATCCCCCGCAATCACATTTCTTATCC |
| pGADT7-PpPGIP1-R (SEQ ID NO: 8) | *ACGATTCATCTGCAG*CTCGAGTTATTTG |

Note: The sequence in italic represents a homologous sequence of the vector; and the bolded sequence represents a restriction site, including BamHI, PstI, BamHI, and XhoI in sequence.

A PCR amplification system was of 25 μL, including: 2 μL of cDNA, 12.5 μL of 2× Phanta Max Master Mix, 1 μL of each of upstream and downstream primers, and 8.5 μL of ddH$_2$O. A PCR amplification procedure for the target fragment PpPGIP1 was as follows: pre-denaturation at 95° C. for 3 min; denaturation at 95° C. for 15 s, annealing at 55° C. for 15 s, and extension at 72° C. for 1 min (35 cycles); and complete extension at 72° C. for 5 min. A PCR amplification procedure for the target fragment PpVIN2 was as follows: pre-denaturation at 95° C. for 3 min; denaturation at 95° C. for 15 s, annealing at 55° C. for 15 s, and extension at 72° C. for 2 min and 30 s (35 cycles); and complete extension at 72° C. for 5 min.

According to the Clon Express® II recombination reaction system, an amount of each component in the recombination reaction was calculated based on concentrations of recovered products of a vector and an inserted fragment to complete the recombination reaction. PpVIN2 was ligated to a bait vector pGBKT7 to obtain a recombinant plasmid BD-PpVIN2, and PpPGIP1 was ligated to a prey vector pGADT7 to obtain a recombinant plasmid AD-PpPGIP1.

According to the requirements of DH5a Competent Cell (CWBIO, Beijing, China), the recombinant plasmids AD-PpPGIP1 and BD-PpVIN2 were each transformed into E. coli DH5α through thermal shock; then the E. coli was coated on an LB-Amp/kana plate that was evenly coated with X-Gal and IPTG, and then invertedly cultivated overnight at 37° C.; single clones were picked for colony PCR identification; and positive clones with the target fragment were screened out and sent to Sangon Biotech (Shanghai) Co., Ltd. for sequencing. Confirmed positive clones were subjected to expanded cultivation, and plasmid extraction was conducted to obtain the prey recombinant plasmid AD-PpPGIP1 and the bait recombinant plasmid BD-PpVIN2.

2. Detection of Toxicity and Self-Activation of the Bait Plasmid

Bait plasmid toxicity detection: The bait plasmid pGBKT7-PpVIN2 and an empty vector pGBKT7 were each transformed into Y2H Gold yeast competent cells, the transformed competent cells were each coated on an SD/-Trp-deficient medium and invertedly cultivated in an incubator at 30° C. for 3 d to 5 d, and then the colony growth on the plate was observed.

Bait plasmid self-activation detection: The bait plasmid pGBKT7-PpVIN2 and an empty vector pGADT7 were co-transformed into Y2H Gold yeast competent cells, the transformed competent cells were coated on SD/-Trp/-Leu, S. Dak./-Trp/-Leu/-His, and SD/-Trp/-Leu/-His/-Ade-deficient media and invertedly cultivated in an incubator at 30° C. for 3 d to 5 d, and then the colony growth on the plate was observed.

3. Co-Transformation of Recombinant Plasmids and Identification of Interacting Protein Fusions According to the lithium acetate (LiAc) transformation method, the bait and prey vectors were co-transformed with the heat-denatured salmon sperm DNA (carrier DNA) into a yeast strain Y2H Gold (Yeastmaker™, Clontech), and BD-53+AD-T and BD-Lam+AD-T (both of which were provided by Yeastmaker™, Clontech) were used as a positive control group and a negative control group, respectively. Then the transformed yeast cells were cultivated on a DDO medium (SD-Leu/-Trp medium) at 30° C. for 2 d to 3 d. Finally, positive colonies were transferred to a QDO medium (SD-Leu/-Trp/-Ade/-His medium) and a QDO/A/X medium (QDO medium with 200 ng/mL Aureobasidin A and 40 μg/mL Xa-Gal) and cultivated at 30° C. for 2 d to 3 d.

According to the growth state and chromogenic reaction, the possible interaction between PpVIN2 and PpPGIP1 was verified.

Figure 1:
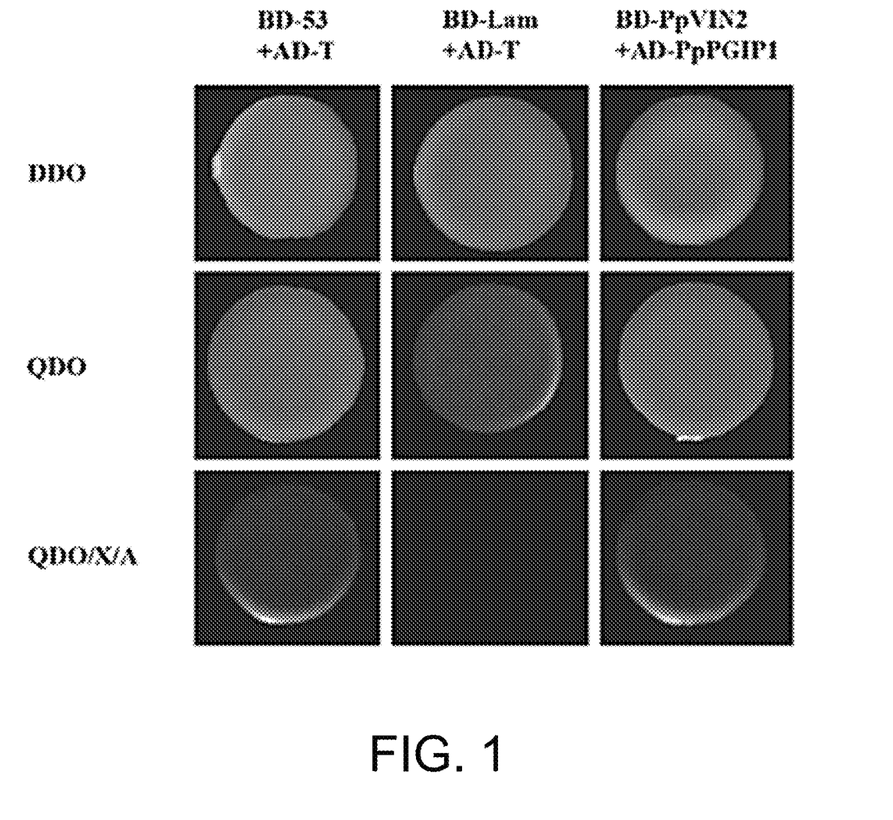
FIG. 1 shows the confirmation of an Y2H system that there is a protein-protein interaction relationship between PpPGIP1 and PpVIN2, where positive control group: BD-53+AD-T; negative control group: BD-Lam+AD-T; and experimental group: BD-PpVIN2+AD-PpPGIP1.

Results were shown in FIG. 1, and it can be seen that the yeast cells co-transformed with bait vector BD-PpVIN2+ prey vector AD-PpPGIP1, BD-53+AD-T, and BD-Lam+ AD-T all could normally grow in the auxotrophic plate DDO, indicating that fusion proteins were successfully transformed into the yeast cell Y2H Gold. In addition, the yeast strains co-transformed with the experimental group BD-PpVIN2+AD-PpPGIP1 and the positive control group BD-53+AD-T could grow normally on the QDO plate, and the co-transformants were all blue on the QDO-X-A plate. The yeast strain co-transformed with the negative control group BD-Lam+AD-T could not grow normally in the QDO medium and appeared like rusty red dead bacteria, and failed to present blue in the QDO-X-A medium. The results showed that the PpPGIP1 and PpVIN2 activated ADE2, HIS3, and MEL1 reporter genes in the yeast genome through protein-protein interaction. This result confirmed that there was protein-protein interaction between the prey protein PpPGIP1 and the bait protein PpVIN2.

Specific Example 3

The PpPGIP1 silencing in peach through *Agrobacterium* transient transformation and VIGS significantly inhibited the VIN activity.

The test variety "Yulu" honey peach ("*Prunus persica* L. Batsch") was picked from the Fenghua Honey Peach Research Institute of Ningbo City, Zhejiang Province. Mature-green-stage peaches that were uniform in size and had no disease, insect, and mechanical damage were selected for *Agrobacterium* infection.

1. In order to improve the efficiency of silencing and reduce the possibility of non-target genes being silenced, the online software SGN VIGS (https://vigs.solgenomics.net/) was used for PpPGIP1 (Gene ID: LOC18769194), to subclone a predicted specific silencing sequence (300 bp) for the target gene PpPGIP1 into a pTRV2 vector to obtain a recombinant vector pTRV2-PpPGIP1, and pTRV1+pTRV2 was adopted as the control group.

Construction and identification of the recombinant vector pTRV2-PpPGIP1: The online website NCBI-PRIMER (https://www.ncbi.nlm.nih.gov/tools/primer-blast/) was used to design specific amplification primers for the peach PpPGIP1 (Gene ID: LOC18769194), and the primers each are flanked with an appropriate restriction site and a homologous sequence of an expression vector (Table 2).

TABLE 2

Primer sequences for constructing the recombinant vector pTRV2-PpPGIP1

| Primer | Sequence |
| --- | --- |
| pTRV2-PpPGIP1-F (SEQ ID NO: 9) | AAGGTTACCGAATTCTCTAGAGACCCCT ACGTCTTGGCCTC |
| pTRV2-PpPGIP1-R (SEQ ID NO: 10) | TGTCTTCGGGACATGCCCGGGCTTGAGT TGGCTGAGGAAGTCAG |

Note: The sequence in italic represents a homologous sequence of the vector; and the bolded sequence represents a restriction site, including XbaI and SmaI in sequence.

A PCR amplification system was of 25 μL, including: 1 μL of cDNA, 12.5 μL of 2× Taq Master Mix, 1 μL of each of upstream and downstream primers, and 9.5 μL of ddH$_2$O. A PCR amplification procedure for the target fragment PGIP was as follows: pre-denaturation at 95° C. for 3 min; denaturation at 95° C. for 15 s, annealing at 59° C. for 15 s, and extension at 72° C. for 1 min (35 cycles); and complete extension at 72° C. for 5 min.

According to the Clon Express®II recombination reaction system, an amount of each component in the recombination reaction was calculated based on concentrations of recovered products of a vector and a target fragment to complete the recombination reaction. PpPGIP1 was ligated to an expression vector pTRV2 to obtain a recombinant vector pTRV2-PpPGIP1.

According to the requirements of DH5a Competent Cell (CWBIO, Beijing, China), the recombinant vector pTRV2-PGIP was transformed into *E. coli* DH5a through thermal shock; then the *E. coli* was coated on an LB/kana plate that was evenly coated with X-Gal and IPTG, and then invertedly cultivated overnight at 37° C.; single clones were picked for colony PCR identification; and positive clones with the target fragment were screened out and sent to Sangon Biotech (Shanghai) Co., Ltd. for sequencing to obtain a PpPGIP1-specific silencing sequence (300 bp), which matched the peach genome data and was shown as follows (SEQ ID NO: 11):

GACCCCTACGTCTTGGCCTCATGGGACCCAGAGACAGACTGCTGTGACTG

GTACTCTGTCACCTGTGACTCCACCACAAACCGCGTCAACTCCCTCACCC

TCTTCTCCGGGGGACTCTCCGGTCAAATTCCGACCCAAGTCGGTGACTTG

CCGTATCTTGAAACACTTGAGTTTCACAAGCAACCCAATCTTACCGGACC

AATCCAACCCTCCATTGCCAAGCTTAAGCGCCTCAAGGAGCTGCGCCTCA

GCTGGACCAACATCTCCGGCTCTGTCCCTGACTTCCTCAGCCAACTCAAG.

2. *Agrobacterium* transformed with the recombinant plasmid was used to infect peach.

The recombinant plasmid carrying the target gene fragment and the empty vector were each transformed into *Agrobacterium tumefaciens* GV3101 through freezing and thawing. The *Agrobacterium tumefaciens* was cultivated in an LB solid medium (kan, 50 μg/mL; Gen, 50 μg/mL; and rif, 50 μg/mL) at 28° C. for 2 d to 3 d, and then single clones were picked and activated in a fresh LB liquid medium (kan, 50 μg/mL; Gen, 50 μg/mL; and rif, 50 μg/mL) at 28° C. for 12 h to 16 h, and then cultivated in a fresh LB liquid medium (kan, 50 μg/mL; rif, 50 μg/mL; MES, 10 mM; and AS, 40 mM) at 28° C. and 200 rpm under shaking for 16 h to 24 h until OD600 was 0.8 to 1.0. A resulting bacterial suspension was centrifuged at room temperature and 5,000 g for 10 min to obtain bacteria, and a resulting supernatant was discarded. The bacteria were resuspended in an osmotic buffer (10 mM MgCl$_2$; 10 mM MES, pH 5.6; and 200 μM AS), OD600 was adjusted to 1.0, and then a resulting suspension stood in the dark for 3 h.

The suspension was injected with a sterile syringe into the sunny side and the night side of the "Yulu" peach, where a needle tip was at about 1 cm below the peel and did not touch the peach pit; and infected peaches were stored at a temperature of 20° C. and a humidity of 85% to 90%. One group of peaches were injected with a suspension of GV3101-pTRV1 and GV3101-pTRV2-PpPGIP1 in a volume ratio of 1:1, and the other group of peaches were injected with a suspension of GV3101-pTRV1 and GV3101-pTRV2 in a volume ratio of 1:1. 7 d and 10 d after the peaches were infected, samples were collected for all peaches and stored at −80° C.

3. Analysis of the Phenotypes and the Basic PpPGIP1 Expression of Peaches Undergoing *Agrobacterium* Transient Transformation Results were shown in FIG. 2. On day 10 after the *Agrobacterium* infection, the infected area on the surface of the peach was darkened, presenting a blue-green color; and after the peel was removed, it was found that the uninfected area was normal white, but the infected area was light green. qPCR analysis showed that the expression level of PpPGIP1 in the GV3101-pTRV1+pTRV2-PpPGIP1 group was significantly lower than that in the control group GV3101-pTRV1+pTRV2 after infected peaches were stored at 20° C. for 7 d and 10 d. The expression level of the PpPGIP1 gene was reduced by 10% and 34% compared with the control group, indicating that the PpPGIP1 gene in peach was effectively silenced, and the system for silencing PpPGIP1 in peach through *Agrobacterium* transient transformation was successfully constructed.

Figure 2:
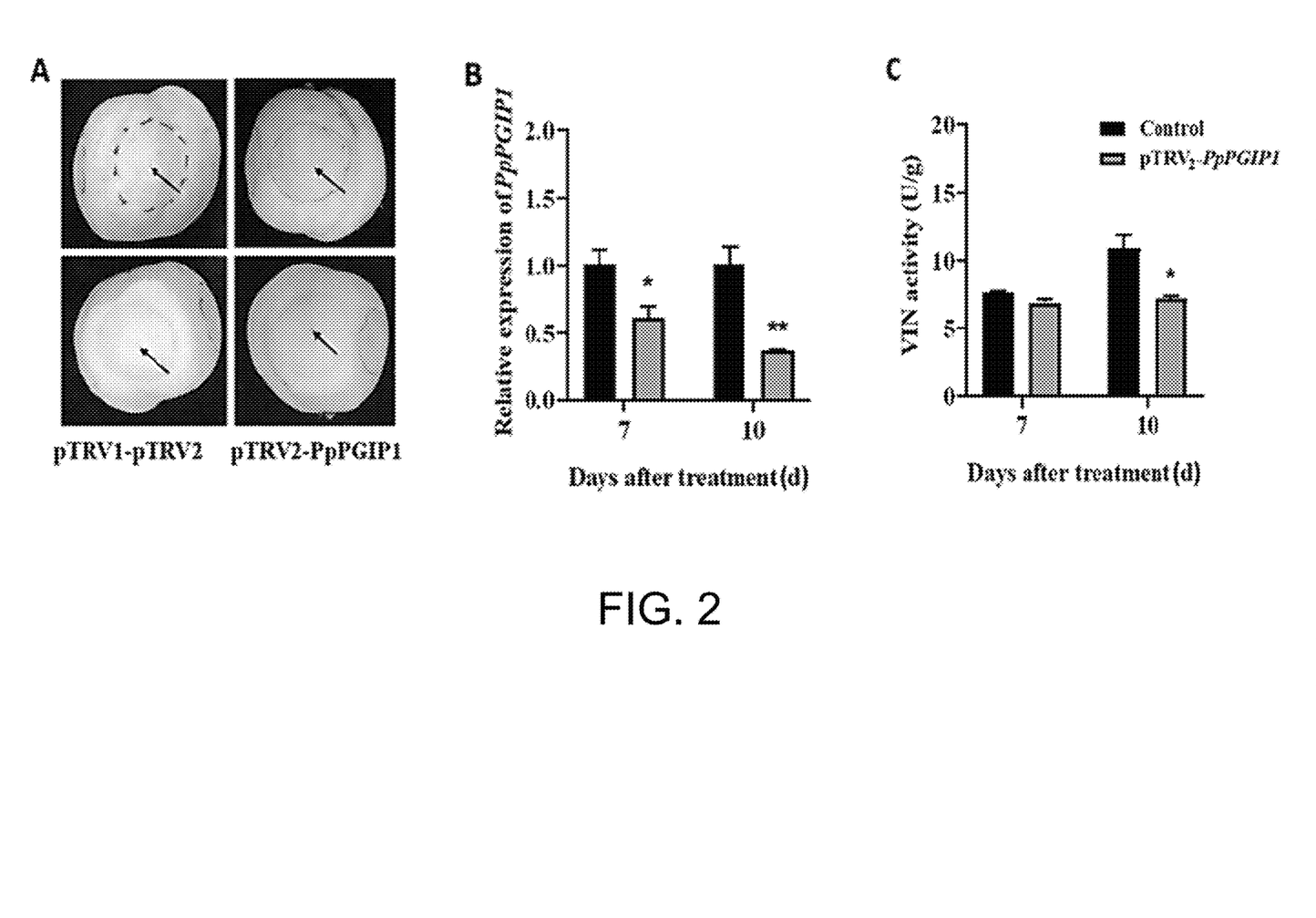
FIG. 2 shows the inhibition of the VIN activity by silencing PpPGIP1 (A, B, and C) in peach through *Agrobacterium* transient transformation, where (A) shows peach phenotypes after *Agrobacterium* infection; (B) shows the PpPGIP1 expression analysis after *Agrobacterium* transient transformation; and (C) shows the effect of successful *Agrobacterium* transient transformation on the VIN activity.

4. Analysis of VIN Activity in Peaches in which PpPGIP1 was Silenced Through *Agrobacterium* Transient Transformation As shown in FIG. 2, compared with the control group, the VIN activity in the experimental group with silenced PpPGIP1 was reduced by 10% and 34% on days 7 and 10, respectively, indicating that the effective inhibition of PpPGIP1 in peach could significantly reduce the VIN activity.

The above description does not limit the present invention, and the present invention is not limited to the above examples. Variations, modifications, additions, or replacements made by those of ordinary skill in the art within the essential scope of the present invention should also fall within the protection scope of the present invention.

What is claimed is:

1. A method of conferring antifreeze in a peach, comprising:
    introducing a virus-induced *Prunus persica* polygalacturonase-inhibiting protein 1 (PpPGIP1) gene silencing vector in the peach; and
    reducing an expression level of a PpPGIP1 gene by the virus-induced PpPGIP1 gene silencing vector to reduce a *Prunus persica* vacuolar invertase 2 (PpVIN2) activity and decomposition of a sucrose in the peach,
    wherein the PpPGIP1 gene comprises the nucleotide sequence shown in of SEQ ID NO: 1,
    wherein the steps for introducing the virus-induced PpPGIP1 gene silencing vector in the peach comprise:
        designing and amplifying a silencing fragment sequence of the PpPGIP1 gene;
        subcloning the silencing fragment sequence into a first virus-induced gene silencing vector to obtain a recombinant vector;
        respectively transforming the recombinant vector and a second virus-induced gene silencing vector into *Agrobacterium* to obtain a first transformant and a second transformant; and
        infecting the first transformant and the second transformant into the peach to introduce the virus-induced PpPGIP1 gene silencing vector in the peach.

2. The method according to claim 1, wherein the step for introducing the virus-induced PpPGIP1 gene silencing vector in the peach comprises an *Agrobacterium*-mediated transient transformation.

3. A method of conferring PpVIN2 inhibition in a peach, comprising:
    introducing a virus-induced PpPGIP1 gene silencing vector in a peach; and
    reducing an expression level of a PpPGIP1 gene by the virus-induced PpPGIP1 gene silencing vector to reduce a PpVIN2 activity in the peach,
    wherein the PpPGIP1 gene comprises the nucleotide sequence of SEQ ID NO: 1,
    wherein the steps for introducing the virus-induced PpPGIP1 gene silencing vector in the peach comprise:
        designing and amplifying a silencing fragment sequence of the PpPGIP1 gene;
        subcloning the silencing fragment sequence into a first virus-induced gene silencing vector to obtain a recombinant vector;
        respectively transforming the recombinant vector and a second virus-induced gene silencing vector into *Agrobacterium* to obtain a first transformant and a second transformant; and
        infecting the first transformant and the second transformant into the peach to introduce the virus-induced PpPGIP1 gene silencing vector in the peach.

4. The method according to claim 3, wherein a method the step for introducing the virus-induced PpPGIP1 gene silencing vector in the peach comprises an *Agrobacterium*-mediated transient transformation.

* * * * *